(12) United States Patent
Boucher, Jr.

(10) Patent No.: US 6,214,536 B1
(45) Date of Patent: Apr. 10, 2001

(54) METHOD OF DETECTING LUNG DISEASE

(75) Inventor: Richard C. Boucher, Jr., Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 09/433,757

(22) Filed: Nov. 4, 1999

Related U.S. Application Data

(63) Continuation of application No. 08/776,772, filed as application No. PCT/US96/12377 on Jul. 24, 1996, now Pat. No. 6,133,247, and a continuation-in-part of application No. 08/509,052, filed on Jul. 31, 1995, now Pat. No. 5,628,984.

(51) Int. Cl.$^7$ ............................... C12Q 1/00; C12Q 1/48
(52) U.S. Cl. .................... 435/4; 435/15; 514/50; 424/45
(58) Field of Search ........................ 435/4, 14; 514/50; 424/45

(56) References Cited

U.S. PATENT DOCUMENTS

| | | |
|---|---|---|
| 3,313,813 | 4/1967 | Cragoe et al. ............................ 435/4 |
| 4,132,600 | 1/1979 | Plotkin et al. .................... 195/103.5 |
| 4,501,729 | 2/1985 | Boucher et al. ........................ 424/45 |
| 4,950,477 | 8/1990 | Schmitt et al. ......................... 424/43 |
| 5,292,498 | 3/1994 | Boucher, Jr. ........................... 424/45 |
| 5,420,116 | 5/1995 | Puchelle et al. ........................ 514/47 |
| 5,470,838 | 11/1995 | Von Borstel et al. ................. 514/50 |
| 5,567,689 | 10/1996 | Sommadossi et al. ................ 514/50 |
| 5,628,984 | * 5/1997 | Boucher, Jr. ............................ 424/45 |
| 5,656,256 | 8/1997 | Boucher et al. ....................... 424/45 |

FOREIGN PATENT DOCUMENTS

| | | |
|---|---|---|
| 2571257 | 4/1986 | (FR) . |
| 1 055 465 | 1/1967 | (GB) . |
| WO 92/11016 | 8/1992 | (WO) . |
| WO 94/08593 | 4/1994 | (WO) . |
| WO 96/18385 | 5/1996 | (WO) . |

OTHER PUBLICATIONS

Boucher et al.; Mechanisms and Therapeutic Actions of Uridine Triphosphate in the Lung, *Adenosine and Adenine Nucleotides Mol. Biol. To Integr. Physiol.* (Proc. Int. Symp.) 5$^{th}$ 1994 (Pub. 1995), 525–32, edited by Belardinelli et al.

Boucher et al.; Mechanisms and Therapeutic Actions of Uridine Triphosphate in the Lung, *Chem Abstracts,* 124 Nov. 20, 1995, Abstract No. 274934z.

Knowles, et al.; Activation by Extracellular Nucleotides of Chloride Secretion in the Airway Epithelia of Patients with Cystic Fibrosis, *The New England Journal of Medicine,* 325:533–538 (1991).

Boucher et al.; Mechanisms and Therapeutic Actions of Uridine Triphosphate in the Lung, *Adenosine and Adenine Nucleotides Mol. Biol. To Integr. Physiol.* (Proc. Int. Symp.) 5$^{th}$ 1994 (Pub. 1995), 525–32, edited by Belardinelli et al.

K.N. Olivier, Acute Safety and Effects on Mucociliary Clearance of Aerosolized Clearance of Aerosolized Uridine 5'–Triphosphate ± Amiloride in Normal Human Adults, *Am. J. Respir. Crit. Care.*

* cited by examiner

*Primary Examiner*—Louise N. Leary
(74) *Attorney, Agent, or Firm*—Myers Bigel Sibley & Sajovec

(57) ABSTRACT

A method of facilitating the obtaining of a mucus sample from at least one lung of a subject comprises administering to at least one lung of the subject, in an amount effective to hydrate lung mucous secretions and/or stimulate cilia beat frequency therein, uridine 5'-triphosphate, an active analog thereof, or a pharmaceutically acceptable salt of either thereof, and, optionally, concurrently administering to said at least one lung a physiologically acceptable salt in an amount effective to hydrate lung mucus secretions therein. A sputum or mucus sample is then collected from said at least one lung, which sample can then be analyzed for lung disease. Pharmaceutical compositions useful for carrying out the method comprise UTP or a salt thereof, alone or in combination with a physiologically acceptable salt, or a pharmaceutically acceptable salt of either thereof. The composition may be a liquid/liquid suspension composition or a dry powder composition.

11 Claims, No Drawings

METHOD OF DETECTING LUNG DISEASE

RELATED APPLICATIONS

This application is a continuation of U.S. application Ser. No. 08/776,772 filling date Jan. 22, 1997, U.S. Pat. No. 6,133,247, which is a 371 of PCT/US96/12377 filling date Jul. 24, 1996, and a continuation-in-part of U.S. patent application Ser. No. 08/509,052 filling date Jul. 31, 1995 now U.S. Pat. No. 5,628,984.

This invention was made with Government support under grant number HL-SPO1-34322 from the National Institutes of Health (NIH). The Government has certain rights to this invention.

FIELD OF THE INVENTION

This application concerns lung diagnostic assays in general, and particularly concerns a lung diagnostic assay in which lung mucus secretions are hydrated to facilitate collection thereof.

BACKGROUND OF THE INVENTION

The analysis of sputum samples is particularly important in the treatment and diagnosis of many lung disorders, including lung cancer and tuberculosis (TB).

In particular, microbial infections of the lung are a serious problem in patients afflicted with acquired immune deficiency syndrome (AIDS). Two particularly problematic infections are *Pneumocystis carinii* pneumonia infections and mycobacterial infections.

*Pneumocystis carinii* pneumonia infections are typically referred to as "PCP" infections. It is now estimated that approximately 70 percent of patients afflicted with AIDS will contract this disease. PCP may be treated with pentamidine isethionate, but an unfortunate side effect of this treatment is its toxicity. Accordingly, there is a continued need for techniques which permit the rapid and convenient screening of AIDS patients for this disease, and for the rapid, early, and accurate diagnosis thereof.

Mycobacteria are a large, diverse, and widely distributed family of aerobic, nonsporulating, nonmotile bacilli that have a high cell-wall lipid content and a slow growth rate. Some Mycobacteria are harmless, while others are significant pathogens. The pathogenic Mycobacterium include *M. tuberculosis*, responsible for tuberculosis, as well as non-tuberculosis Mycobacteria such as *M. avium*, responsible for *Mycobacterium Avium* complex infections.

SUMMARY OF THE INVENTION

A first aspect of the present invention is a method of facilitating the obtaining of a mucus sample from at least one lung of a subject. The method comprises administering a physiologically acceptable salt to at least one lung of the subject in an amount effective to hydrate lung mucus secretions therein, and concurrently administering to said at least one lung of the subject, in an amount effective to hydrate lung mucous secretions, and/or stimulate mucus secretions therein, and/or stimulate ciliary beat frequency therein, a compound of Formula (I) below, or a pharmaceutically acceptable salt thereof:

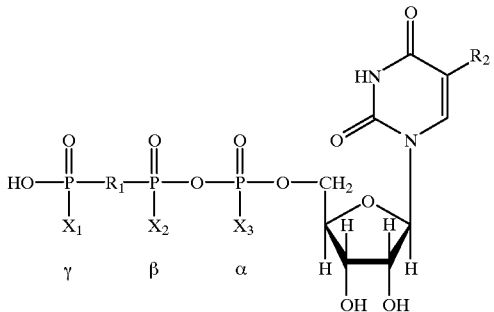

(I)

wherein:

$X_1$, $X_2$, and $X_3$ are each independently selected from the group consisting of OH and SH;

$R_1$ is selected from the group consisting of O, imido, methylene, and dihalomethylene; and $R_2$ is selected from the group consisting of H and Br.

The method is accompanied or followed by the step of collecting a mucus sample from said at least one lung of said subject (e.g., by said subject expectorating a sputum sample).

Also disclosed is a method of facilitating the obtaining of a mucus sample from at least one lung of a subject, comprising administering to at least one lung of said subject, in an amount effective to hydrate lung mucous secretions, and/or stimulate mucus secretions therein, and/or stimulate ciliary beat frequency therein, a compound of Formula (I) as given above, or a pharmaceutically acceptable salt thereof, and then collecting a mucus sample from said at least one lung of said subject. The mucus samples collected may then be analyzed for the presence or absence of lung disease (e.g., microbial infection, cancer, etc.) in said subject.

A second aspect of the present invention is pharmaceutical composition useful for facilitating the collecting of a mucus sample from at least one lung of a subject, said composition comprising, alone or in combination, a physiologically acceptable salt in an amount effective to hydrate lung mucus secretions; and a compound of Formula (I) as given above, or a pharmaceutically acceptable salt thereof, in an amount effective to hydrate lung mucus secretions. The composition may be a liquid composition or a dry powder composition.

DETAILED DESCRIPTION OF THE INVENTION

Compounds illustrative of the compounds of Formula (I) above (also referred to as "active compounds" herein) include: (a) uridine 5'-triphosphate (UTP); (b) uridine 5'-O-(3-thiotriphosphate) (UTPγS); and (c) 5-bromouridine 5'-triphosphate (5-BrUTP). One preferred compound of Formula (I) above is the UTP analog uridine 5'-O-(3-thiotriphosphate) (or "UTPγS"). These compounds are known or may be made in accordance with known procedures, or variations thereof which will be apparent to those skilled in the art. See generally U.S. Pat. No. 5,292,498 to Boucher; N. Cusack and S. Hourani, *Annals N.Y. Acad. Sci.* 603, 172–181 (G. Dubyak and J. Fedan Eds. 1990). For example, UTP may be made in the manner described in Kenner et al., *J. Chem. Soc.* 1954, 2288; or Hall and Khorana, *J. Chem. Soc.* 76, 5056 (1954). See Merck Index, Monograph No. 9795 (11th Ed. 1989). UTPγS may be made in the manner described in R. S. Goody and F. Eckstein, *J. Am. Chem. Soc.* 93, 6252 (1971).

For simplicity, Formula I herein illustrates uridine triphosphate active compounds in the naturally occurring D configuration, but the present invention also encompasses compounds in the L configuration, and mixtures of compounds in the D and L configurations, unless specified otherwise. The naturally occurring D configuration is preferred.

The active compounds of Formula (I) may be administered by themselves or in the form of their pharmaceutically acceptable salts, e.g., an alkali metal salt such as sodium or potassium, an alkaline earth metal salt, or an ammonium and tetraalkyl ammonium salt, $NX_4^+$ (wherein X is a $C_{1-4}$ alkyl group). Pharmaceutically acceptable salts are salts that retain the desired biological activity of the parent compound and do not impart undesired toxicological effects.

Amiloride (also known as 3,5,-diamino-6-chloro-N-(diaminomethylene)pyrazinecarboxamide), benzamil (also known as 3,5-diamino-6-chloro-N-(benzylaminoaminomethylene) pyrazinecarboxamide) and phenamil (also known as 3,5-diamino-6-chloro-N-(phenylaminoaminomethylene) pyrazinecarboxamide) are known compounds and are disclosed in U.S. Pat. No. 3,313,813 to E. Cragoe. The terms "amiloride," "benzamil," and "phenamil," as used herein (also referred to as "active compounds" herein); include the pharmaceutically acceptable salts thereof, such as (but not limited to) amiloride hydrochloride, benzamil hydrochloride or phenamil hydrochloride. Amiloride, benzamil or phenamil used to prepare compositions for the present invention may alternatively be in the form of a pharmaceutically acceptable free base of amiloride, benzamil or phenamil. Because the free base of the compound is less soluble than the salt, free base compositions are employed to provide more sustained release of benzamil or phenamil to the lungs.

Physiologically acceptable salts (also sometimes referred to as "active compounds" herein) used to carry out the method of the present invention are those that hydrate lung mucus secretions by facilitating the transport of water from lung endothelial cells into the mucus. Physiologically acceptable salts are salts that retain the desired biological activity of hydrating lung mucus secretions and do not impart undesired toxicological effects. Physiologically acceptable salts are typically chloride salts, such as sodium chloride, potassium chloride, choline chloride, and N-methyl-D-glucamine chloride. Sodium chloride is currently preferred. These salts may be provided in the form of a dry respirable powder (discussed below) or as an aqueous solution.

The present invention is concerned primarily with the treatment of human subjects. Subjects may or may not be cystic fibrosis patients. The present invention may also be employed for the treatment of other mammalian subjects, such as dogs and cats, for veterinary purposes.

The active compounds disclosed herein may be administered to the lung(s) of a subject by any suitable means. As used herein, the word "concurrently" means sufficiently close in time to produce a combined effect (that is, concurrently may be simultaneously, or it may be two or more events occurring within a short time period before or after each other). By "at least one lung" is meant that administration of active compounds may be to one or both lungs of the subject, but where administration is to only one lung, then administration of the various active compounds is to the same lung.

Active compounds are preferably administered by administering an aerosol suspension of respirable particles comprised of the active compound or active compounds, which the subject inhales. The active compound can be aerosolized in a variety of forms, such as, but not limited to, dry powder inhalants, metered dose inhalants, or liquid/liquid suspensions. The respirable particles may be liquid or solid. The particles may optionally contain other therapeutic ingredients such as amiloride, benzamil or phenamil, with the selected compound included in an amount effective to inhibit the reabsorption of water from airway mucous secretions, as described in U.S. Pat. No. 4,501,729 (applicant specifically intends the disclosure of this and all other patent references cited herein be incorporated herein by reference).

The particulate pharmaceutical composition may optionally be combined with a carrier to aid in dispersion or transport. A suitable carrier such as a sugar (i.e., lactose, sucrose, trehalose, mannitol) may be blended with the active compound or compounds in any suitable ratio (e.g., a 1 to 1 ratio by weight).

Particles comprised of active compound for practicing the present invention should include particles of respirable size: that is, particles of a size sufficiently small to pass through the mouth or nose and larynx upon inhalation and into the bronchi and alveoli of the lungs. In general, particles ranging from about 1 to 10 microns in size (more particularly, less than about 5 microns in size) are respirable. Particles of non-respirable size which are included in the aerosol tend to deposit in the throat and be swallowed, and the quantity of non-respirable particles in the aerosol is preferably minimized. For nasal administration, a particle size in the range of 10–500 $\mu$m is preferred to ensure retention in the nasal cavity.

Liquid pharmaceutical compositions of active compound for producing an aerosol may be prepared by combining the active compound with a suitable vehicle, such as sterile pyrogen free water. The hypertonic saline solutions used to carry out the present invention are preferably sterile, pyrogen-free solutions, comprising from one to fifteen percent (by weight) of the physiologically acceptable salt, and more preferably from three to seven percent by weight of the physiologically acceptable salt. Where compounds of Formula (I) or the pharmaceutically acceptable salts thereof are included in the hypertonic saline solution, they are typically included in a concentration ranging from about $10^{-4}$M to about $10^{-1}$M, and more preferably in a concentration ranging from about $10^{-2}$M to about $10^{-1}$M. Other therapeutic compounds such as amiloride, benzamil or phenamil-may optionally be included (when such compounds are included, the saline solution is preferably not more than 0.3 percent by weight of the physiologically acceptable salt, and more preferably is 0.12 percent by weight of the physiologically acceptable salt).

Solid particulate compositions containing respirable dry particles of micronized active compound may be prepared by grinding dry active compound with a mortar and pestle, and then passing the micronized composition through a 400 mesh screen to break up or separate out large agglomerates. The active compound may be formulated alone (i.e., the solid particulate composition may consist essentially of the active compound) or in combination with a dispersant, diluent or carrier, such as sugars (i.e., lactose, sucrose, trehalose, mannitol) or other acceptable excipients for lung or airway delivery, which may be blended with the active compound in any suitable ratio (e.g., a 1 to 1 ratio by weight). The dry powder solid particulate composition may be obtained by methods known in the art, such as spray-drying, milling, freeze-drying, etc. Again, other therapeutic compounds such as amiloride, benzamil or phenamil may also be included.

Aerosols of liquid particles comprising the active compound may be produced by any suitable means, such as with a pressure-driven jet nebulizer or an ultrasonic nebulizer. See, e.g., U.S. Pat. No. 4,501,729. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w of the formulation, but preferably less than 20% w/w. The carrier is typically water (and most preferably sterile, pyrogen-free water) or a dilute aqueous alcoholic solution, preferably made isotonic, but may be hypertonic with body fluids by the addition of, for example, sodium chloride. Optional additives include preservatives if the formulation is not made sterile, for example, methyl hydroxybenzoate, antioxidants, flavoring agents, volatile oils, buffering agents and surfactants.

Aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing a predetermined metered dose of a medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation. A second type of illustrative aerosol generator comprises a metered dose inhaler. Metered dose inhalers are pressurized aerosol dispensers, typically containing a suspension or solution formulation of the active ingredient in a liquified propellant. During use these devices discharge the formulation through a valve adapted to deliver a metered volume, typically from 10 to 200 $\mu$l, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol, surfactants, such as oleic acid or sorbitan trioleate, antioxidants and suitable flavoring agents.

Any propellant may be used in carrying out the present invention, including both chlorofluorocarbon-containing propellants and non-chlorofluorocarbon-containing propellants. Thus, fluorocarbon aerosol propellants that may be employed in carrying out the present invention including fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Examples of such propellants include, but are not limited to: $CF_3$—CHF—$CF_2H$; $CF_3$—$CH_2$—$CF_2H$; $CF_3$—CHF—$CF_3$; $CF_3$—$CH_2$—$CF_3$; $CF_3$—CHCl—$CF_2Cl$; $CF_3$—CHCl—$CF_3$; cy—C($CF_2)_3$—CHCl; $CF_3$—CHCl—$CH_2Cl$; $CF_3$—CHF—$CF_2Cl$; $CF_3$—CHCl—CFHCl; $CF_3$—CFCl—CFHCl; $CF_3$—$CF_2$—$CF_2H$; $CF_3$—$CF_2$—$CH_3$; $CF_2H$—$CF^2$—$CFH_2$; $CF_3$—$CF_2$—$CFH_2$; $CF_3$—$CF_2$—$CH_2Cl$; $CF_2H$—$CF_2$—$CH_3$; $CF_2H$—$CF_2$—$CH_2Cl$; $CF_3$—$CF_2$—$CF_2$—$CH_3$; $CF_3$—$CF_2$—$CF_2$—$CF_2H$; $CF_3$—CHF—CHF—$CF_3$; $CF_3$—O—$CF_3$; $CF_3$—O—$CF_2H$; $CF_2H$—H—O—$CF_2H$; $CF_2H$—O—$CFH_2$; $CF_3$—O—$CH_3$; $CF_3$—O—$CF_2$—$CF_2H$; $CF_3$—O—$CF_2$—O—$CF_3$; cy—$CF_2$—$CF_2$—O—$CF_2$—; cy—CHF—$CF_2$—O—$CF_2$—; cy—$CH_2$—$CF_2$—O—$CF_2$—; cy—$CF_2$—O—$CF_2$—O—$CF_2$—; $CF_3$—O—$CF_2$—Br; $CF_2H$—O—$CF_2$—Br; and mixtures thereof, where "cy" denotes a cyclic compound in which the end terminal covalent bonds of the structures shown are the same so that the end terminal groups are covalently bonded together. Particularly preferred are hydrofluoroalkanes such as 1,1,1,2-tetrafluoroethane (propellant 134a) and heptafluoropropane (propellant 227). A stabilizer such as a fluoropolymer may optionally be included in formulations of fluorocarbon propellants, such as described in U.S. Pat. No. 5,376,359 to Johnson.

The aerosol, whether formed from solid or liquid particles, may be produced by the aerosol generator at a rate of from about 10 to 150 liters per minute, more preferably from about 30 to 150 liters per minute, and most preferably about 60 liters per minute. Aerosols containing greater amounts of medicament may be administered more rapidly. Typically, each aerosol may be delivered to the patient for a period from about 30 seconds to about 20 minutes, with a delivery period of about five to ten minutes being preferred.

The dosage of the compound of Formula (I), or the pharmaceutically acceptable salt thereof, will vary depending on the condition being treated and the state of the subject, but generally may be an amount sufficient to achieve dissolved concentrations of active compound on the airway surfaces of the subject of from about $10^{-9}$ to about $10^{-2}$ Moles/liter or even $10^{-1}$ Moles/liter, more preferably from about $10^{-5}$ to about $10^{-1}$ Moles/liter, and most preferably from about $10^{-4}$ to about $10^{-3}$ to about $10^{-1}$ moles/liter. Depending upon the solubility of the particular formulation of active compound administered, the daily dose may be divided among one or several unit dose administrations.

When the sputum sample is subjected to cytological, bacterial or DNA analysis for detecting infectious microbial species therein, the sputum sample may first be digested with a liquefying agent, such as N-acetyl-L-cystein (NALC) and sodium hydroxide.

As noted above, the present invention is particularly useful for collecting mucus samples which are used for detecting *Pneumocystis carinii* pneumonia and Mycobacteria infections. The term "Mycobacteria" as used herein has its conventional meaning in the art referring to acid-fast, non-motile, rod shaped bacteria. See generally B. Davis et al., *Microbiology*, 724–742 (#d. Ed. 1980). All generally belong to the family Mycobacteriaceae. By way of example, the mycobacteria include, but are not limited to, *Mycobacterium africanum, M. avium, M. bovis, M. bovis-BCG, M. chelonae, M. fortuitum, M. gordonae, M. intracellulae, M. kansasii, M. leprae, M. microti, M. paratuberculosis, M. scrofulaceum,* and *M. tuberculosis*. The present invention is useful in diagnosing both tuberculosis and non-tuberculosis Mycobacteria, and is useful in diagnosing *M. avium* complex infections.

The present invention is explained in greater detail in the following non-limiting Examples.

EXAMPLE 1

Delivery of UTP Followed by Hypertonic Saline

A subject is caused to inhale an aerosol of UTP solution ($10^{-2}$M UTP in 0.9% (by weight) sterile pyrogen-free saline solution) delivered by a Pari LC Plus nebulizer for 10 minutes. Immediately afterwards, the subject is caused to inhale an aerosol of hypertonic saline solution (3% sterile pyrogen-free saline solution), delivered by a nebulizer for 10 minutes. During inhalation of the aerosols and after inhalation of the aerosols, the subject is encouraged to cough, and all sputum is collected during aerosol inhalation and over a 20 minute interval following cessation of aerosol inhalation. The sputum is captured in a plastic sputum container. The sputum so obtained is analyzed for content pending the clinical requirement, including analyses of cytologies for pulmonary neoplasm, and the presence of infectious agents, for example, *Pneumocystis carinii*, by silver staining and immunofluorescence techniques. The technique is applicable for the diagnoses of other micro-organisms in the lower lung, including bacterial, viral, amd mycoplasma, using culture, immunocytochemical, and molecular (PCR, in situ hybridization) techniques.

EXAMPLE 2

Delivery of UTP with Amiloride

This example is carried out in essentially the same manner as example 1 above, except that the UTP is dissolved in a 0.12% sterile pyrogen-free NaCl solution, and the solution also contains $10^{-2}$M amiloride.

EXAMPLE 3

Delivery of Hypertonic Saline Followed by UTP

This Example is carried out in essentially the same manner as Example 1 above, except that the hypertonic saline solution is delivered first, and the UTP solution is delivered immediately thereafter. Durations of delivery and concentrations remain the same.

EXAMPLE 4

Concurrent Delivery of UTP in Hypertonic Saline

This Example is carried out by modification of Example 1 above, with $10^{-1}$ UTP being diluted in the hypertonic saline solution so that a single solution is delivered to the patient by inhalation of an aerosol generated by a nebulizer for a period of 15 minutes.

EXAMPLE 5

Delivery of UTP Followed by Sample Collection

This procedure is carried out in essentially the same manner as Example 1 above, except that there is no separate administration of a hypertonic saline solution.

A subject is caused to inhale an aerosol of UTP solution ($10^{-2}$M UTP in 0.9% (by weight) sterile pyrogen-free saline solution) delivered by a Pari LC Plus nebulizer for 10 minutes. During inhalation of the aerosol and after inhalation of the aerosol, the subject is encouraged to cough, and all sputum is collected during aerosol inhalation and over a 20 minute interval following cessation of aerosol inhalation. The sputum is captured in a plastic sputum container. The sputum so obtained is analyzed as described in Example 1. The technique is applicable for the diagnoses of other micro-organisms in the lower lung, including bacterial, viral, and mycoplasma, using culture, immunocytochemical, and molecular (PCR, in situ hybridization) techniques.

EXAMPLE 6

Delivery of Solid Particulate UTP

This example is carried out in essentially the same manner as Example 5 above, except the subject is administered a respirable dry powder consisting essentially of solid particulate UTP or a pharmaceutically acceptable salt such as trisodium UTP prepared as described above, or as described in U.S. Pat. No. 5,292,498 to Boucher. A sputum sample is collected from the subject as described in Examples 1 and 5 above, and analyzed as described in Examples 1 and 5 above.

The foregoing examples are illustrative of the present invention, and are not to be construed as limiting thereof. Among other things, volumes, times, and amounts can be varied from those specifically set forth above. Accordingly, the invention is defined by the following claims, with equivalents of the claims to be included therein.

That which is claimed is:

1. A method of facilitating the obtaining of a mucus sample from at least one lung of a subject, comprising:
   administering to said at least one lung of said subject, in an amount effective to hydrate lung mucous secretions and/or stimulate cilia beat frequency therein, a compound of Formula (I) below, or a pharmaceutically acceptable salt thereof:

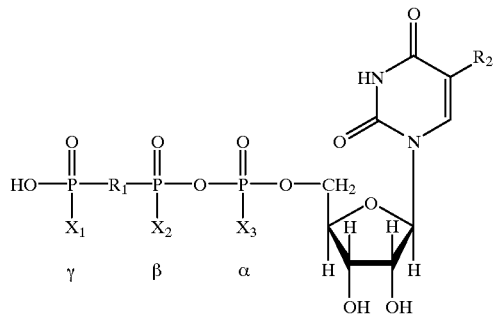

(I)

wherein:
   $X_1$, $X_2$, and $X_3$ are each independently selected from the group consisting of OH and SH;
   $R_1$ is selected from the group consisting of O, imido, methylene, and dihalomethylene; and
   $R_2$ is selected from the group consisting of H and Br; and then collecting a mucus sample from said at least one lung of said subject, wherein said mucus sample is collected by expectoration.

2. The method according to claim 1, further comprising the step of analyzing said collected mucus sample to detect the presence or absence of lung disease in said subject.

3. The method according to claim 2, wherein said analyzing step comprises PCR analysis.

4. The method according to claim 1, wherein said compound of Formula I is administered in a pharmaceutical composition comprising said compound of Formula I in a concentration of $10^{-2}$M in 0.9% saline solution by weight.

5. The method according to claim 2, wherein the analyzing step comprises immunocytochemical analysis.

6. The method according to claim 1, wherein said compound of Formula (I), or said pharmaceutically acceptable salt thereof, is administered in an amount sufficient to achieve concentrations thereof on the airway surfaces of said subject of from about $10^{-9}$ to about $10^{-1}$ Moles/liter.

7. The method according to claim 1, further comprising concurrently administering to said subject a compound selected from the group consisting of amiloride, benzamil and phenamil, and pharmaceutically acceptable salts thereof, in an amount effective to inhibit the reabsorption of water from lung mucous secretions.

8. The method according to claim 1, wherein $X_2$ and $X_3$ are OH.

9. The method according to claim 1, wherein $R_1$ is oxygen.

10. The method according to claim 1, wherein $R_2$ is H.

11. The method according to claim 1, wherein said compound of Formula I is selected from the group consisting of uridine 5'-triphosphate, uridine 5'-O-(3-thiotriphosphate), and the pharmaceutically acceptable salts thereof.

* * * * *